United States Patent
Fujiwara et al.

(10) Patent No.: US 8,263,796 B2
(45) Date of Patent: Sep. 11, 2012

(54) PROCESS FOR PRODUCTION OF CYANOHYDRIN COMPOUND, AND PROCESS FOR PRODUCTION OF α-HYDROXYESTER COMPOUND

(75) Inventors: Naoki Fujiwara, Isumi (JP); Kazuya Nakagawa, Toyama (JP); Yuichiro Kinoshita, Isumi (JP); Koji Midorikawa, Tokyo (JP)

(73) Assignee: Nippoh Chemicals Co., Ltd., Chuo-Ku, Tokyo (JP)

( * ) Notice: Subject to any disclaimer, the term of this patent is extended or adjusted under 35 U.S.C. 154(b) by 217 days.

(21) Appl. No.: 12/734,255

(22) PCT Filed: Oct. 21, 2008

(86) PCT No.: PCT/JP2008/068998
§ 371 (c)(1),
(2), (4) Date: Apr. 21, 2010

(87) PCT Pub. No.: WO2009/054356
PCT Pub. Date: Apr. 30, 2009

(65) Prior Publication Data
US 2010/0256409 A1    Oct. 7, 2010

(30) Foreign Application Priority Data

Oct. 23, 2007 (JP) .................. 2007-275696

(51) Int. Cl.
*C07C 253/30* (2006.01)
*C07C 69/003* (2006.01)

(52) U.S. Cl. ....................... 558/351; 560/129

(58) Field of Classification Search .......... None
See application file for complete search history.

(56) References Cited

U.S. PATENT DOCUMENTS
2008/0214861 A1    9/2008    Kozono et al.

FOREIGN PATENT DOCUMENTS

| | | |
|---|---|---|
| EP | 0 941 984 | 9/1999 |
| GB | 892781 | 3/1962 |
| JP | 164511 | 6/1944 |
| JP | 34-522 | 2/1959 |
| JP | 35-5755 | 5/1960 |
| JP | 36-5869 | 5/1961 |
| JP | 36-11965 | 7/1961 |
| JP | 36-12115 | 7/1961 |
| JP | 43-29574 | 12/1968 |
| JP | 10-025273 | 1/1998 |
| WO | WO 2007/018221 | 2/2007 |

OTHER PUBLICATIONS

Takamura, et al. (2002) "Efficient synthesis of antihypergly cemic (S)α-Aryloxy-β-phenylpropionic acid using a bifunctional asymmetric catalyst" Chem. Pharm. Bull. 50(8):1118-1121.
European Search Report for Application No. 08840797.8 dated Dec. 19, 2011.

*Primary Examiner* — Kamal Saeed
(74) *Attorney, Agent, or Firm* — Harness, Dickey & Pierce, P.L.C.

(57) ABSTRACT

A process according to the present invention for producing a cyanohydrin compound is a process for producing a cyanohydrin compound by performing a reaction between a carbonyl compound such as an aldehyde compound and hydrogen cyanide in the presence of a catalyst, a content of the carbonyl compound in a reaction system being not more than 50 mol % with respect to the cyanohydrin compound. Thus provided is a process for producing a cyanohydrin compound in good yield from an aldehyde compound and hydrogen cyanide.

7 Claims, No Drawings

PROCESS FOR PRODUCTION OF CYANOHYDRIN COMPOUND, AND PROCESS FOR PRODUCTION OF α-HYDROXYESTER COMPOUND

TECHNICAL FIELD

The present invention relates to processes for producing cyanohydrin compounds and processes for producing α-hydroxyester compounds and, in particular, to a process for producing a cyanohydrin compound from a carbonyl compound and hydrogen cyanide and to a process for producing an α-hydroxyester compound with use of such a cyanohydrin compound.

BACKGROUND ART

Cyanohydrin compounds are useful as starting materials for synthesis of various compounds, e.g., for production of α-hydroxyester compounds. As such a process for producing a cyanohydrin compound, a process for achieving a synthesis by cooling and stirring a carbonyl compound including a catalyst and serving as a raw material, supplying hydrogen cyanide slowly thereinto, proceeding with a reaction while removing reaction heat successively (hereinafter referred to as "batch process") is commonly used. The reaction between the carbonyl compound and the hydrogen cyanide is very high in speed and also high in reaction heat. Therefore, the hydrogen cyanide is supplied over a long period of time so that the reaction system is inhibited from abruptly rising in temperature.

Besides the batch process, there have been known processes described in Patent Literatures 1 to 7 for producing cyanohydrin compounds.

For example, Patent Literatures 1 and 2 disclose processes for continuously producing cyanohydrin with use of hydrogen cyanide gas. Patent Literatures 3 and 6 disclose processes for producing acetone cyanohydrin, including continuously supplying hydrogen cyanide into a reaction tower and discharging it out of the reaction tower. Patent Literature 4 describes a process for producing acetone cyanohydrin, including continuously introducing acetone and hydrogen cyanide into a reactor vessel and producing acetone cyanohydrin by use of a difference in specific gravity between the starting materials and the product. Patent Literature 5 describes a process for performing a continuous reaction by causing an anion-exchange resin to exist in a flowing state in a mixed solution of acetone and hydrogen cyanide or a mixed solution of a product of acetone and hydrogen cyanide. Patent Literature 6 discloses a process for producing cyanohydrin, including continuously supplying hydrogen cyanide and an aliphatic carbonyl compound into a reaction tower and discharging them out of the reaction tower. Patent Literature 7 discloses a process for producing acetone cyanohydrin by reacting acetone with hydrogen cyanide in the presence of a basic catalyst in a reactor vessel.

CITATION LIST

Patent Literature 1
Japanese Patent Application Publication, Tokukosho, No. 34-522 B (Publication Date: Feb. 9, 1959)
Patent Literature 2
Japanese Patent Application Publication, Tokukosho, No. 35-5755 B (Publication Date: May 25, 1960)
Patent Literature 3
Japanese Patent Application Publication, Tokukosho, No. 36-5869 B (Publication Date: May 26, 1961)
Patent Literature 4
Japanese Patent Application Publication, Tokukosho, No. 36-11965 B (Publication Date: Jul. 29, 1961)
Patent Literature 5
Japanese Patent Application Publication, Tokukosho, No. 36-12115 B (Publication Date: Jul. 31, 1961)
Patent Literature 6
Japanese Patent Application Publication, Tokukosho, No. 38-6761 B (Publication Date: May 22, 1963)
Patent Literature 7
Japanese Patent Application Publication, Tokukaihei, No. 10-25273 A (Publication Date: Jan. 27, 1998)

SUMMARY OF INVENTION

However, such a process for production through the conventional batch process sometimes results in a decrease in yield of a cyanohydrin compound especially when a carbonyl compound or, in particular, an aldehyde compound is used as a starting material. Further, although Patent Literatures 1, 2, and 6 describe processes for producing cyanohydrin compounds by using carbonyl compounds as starting materials, these disclosed methods give no consideration for such a decrease in yield. Therefore, there has been a demand for the development of a process for producing a cyanohydrin compound in good yield while using an aldehyde compound as a starting material.

The present invention has been made in view of the foregoing problems, and it is an object of the present invention to provide a process for producing a cyanohydrin compound in good yield by reacting an aldehyde with hydrogen cyanide. Further, it is another object of the present invention to provide a process for producing an α-hydroxyester compound with use of a cyanohydrin compound obtained by a production process of the present invention.

As a result of their diligent study to solve the foregoing problems, the inventors have newly found that especially when a cyanohydrin compound is industrially produced, prolonged exposure of the cyanohydrin compound in the presence of a high concentration of aldehyde compound causes the cyanohydrin compound and the aldehyde compound to react to form a by-product and thereby causes a decrease in yield of the cyanohydrin compound. Therefore, the inventors have found that a decrease in yield of the cyanohydrin compound can be prevented by controlling the concentration of the carbonyl compound such as the aldehyde in the reaction liquid. Based on these findings, the inventors have finally accomplished the present invention.

A process according to the present invention for producing a cyanohydrin compound is a process for producing a cyanohydrin compound by performing a reaction between a carbonyl compound and hydrogen cyanide in the presence of a catalyst, a content of the carbonyl compound in a reaction system being not more than 50 mol % with respect to the cyanohydrin compound.

The process thus arranged makes it possible to reduce the content of an unreacted portion of the carbonyl compound in the reaction system, and to therefore inhibit a reaction between the carbonyl compound and the resulting cyanohydrin compound. This makes it possible, as a result, to produce the cyanohydrin compound in better yield even when it takes a long period of time to supply the raw materials. In the present invention, the reaction system refers to a system that is used between (a) mixing the carbonyl compound and the hydrogen cyanide together and (b) stopping the reaction by either isolating the cyanohydrin compound or neutralizing or removing the basic catalyst, or that is used in a reaction in the next step.

Further, in the process according to the present invention for producing a cyanohydrin compound, it is preferable that the carbonyl compound be an aldehyde compound represented by general formula (1):

[Chem. 1]

(1)

wherein $R^1$ is an aryl group or a C1-C10 hydrocarbon group; and $R^1$ is allowed to have a substituent therein and to contain an atom other than carbon in a structure thereof.

The process thus arranged makes it possible to reduce the content of an unreacted portion of the aldehyde compound in the reaction system, and to therefore inhibit a reaction between the aldehyde compound and the resulting cyanohydrin compound. This makes it possible, as a result, to produce the cyanohydrin compound in better yield even when it takes a long period of time to supply the raw materials.

Further, in the process according to the present invention for producing a cyanohydrin compound, it is preferable that the reaction between the hydrogen cyanide and the carbonyl compound be performed by supplying the carbonyl compound into the hydrogen cyanide in the presence of a basic catalyst. The process thus arranged makes, it possible to easily control the concentration of the carbonyl compound in the reaction system.

Further, it is more preferable that the reaction between the hydrogen cyanide and the carbonyl compound be performed by alternately and separately supplying the hydrogen cyanide and the carbonyl compound into a reactor vessel in the presence of the basic catalyst, or it is even more preferable that the reaction between the hydrogen cyanide and the carbonyl compound be performed by simultaneously supplying the hydrogen cyanide and the carbonyl compound into a reactor vessel in the presence of the basic catalyst. The process thus arranged makes it possible to lessen a remaining portion of the hydrogen cyanide in the reaction system, in addition to making it possible to easily control the concentration of the carbonyl compound such as the aldehyde compound in the reaction system so that the concentration falls within a particular range, and therefore makes safe production possible.

It is preferable to simultaneously supply the hydrogen cyanide and the carbonyl compound be into a reactor vessel and to supply the hydrogen cyanide while keep it at 1.00 mol to 1.05 mol with respect to the carbonyl compound. During the supply, the hydrogen cyanide may vary within a range of 0.80 mol to 1.30 mol with respect to the carbonyl compound.

In the process according to the present invention for producing a cyanohydrin compound, it is preferable that the hydrogen cyanide be used in a range of 0.9 to 3.0 mol with respect to 1 mol of the carbonyl compound before the cyanohydrin compound flows out of the reaction system.

In the process according to the present invention for producing a cyanohydrin compound, it is preferable that the catalyst be at least either an organic basic compound or an inorganic basic compound.

In the process according to the present invention for producing a cyanohydrin compound, it is preferable that the catalyst be a compound selected from the group consisting of an amine compound, an aromatic amine compound, an alkali metal compound, a metal alkoxide compound, and an alkaline-earth metal compound.

In the process according to the present invention for producing a cyanohydrin compound, it is preferable that the catalyst be used in a range of 0.001 to 0.1 mol with respect to 1 mol of the hydrogen cyanide.

In the process according to the present invention for producing a cyanohydrin compound, it is preferable, but is not necessary, that a solvent be used in the reaction between the hydrogen cyanide and the carbonyl compound such as the aldehyde compound.

A process according to the present invention for producing an α-hydroxyester compound includes the step of hydrolyzing and esterifying a cyanohydrin compound produced by a production process according to the present invention.

The process thus arranged makes it possible to obtain an intermediate, i.e. a cyanohydrin compound in good yield, in producing an α-hydroxyester compound by using a carbonyl compound such as an aldehyde compound as a starting material, and to therefore obtain the α-hydroxyester compound in good yield.

Additional objects, features, and strengths of the present invention will be made clear by the description below.

DESCRIPTION OF EMBODIMENTS

An embodiment of the present invention is described below in detail.

[Process for Producing a Cyanohydrin Compound]

A process according to the present invention for producing a cyanohydrin compound is a process for producing a cyanohydrin compound by performing a reaction between a carbonyl compound such as an aldehyde compound represented by general formula (1) and hydrogen cyanide in the presence of a catalyst, a content of the carbonyl compound in a reaction system being not more than 50 mol % with respect to the cyanohydrin compound:

[Chem. 2]

(1)

wherein $R^1$ is an aryl group or a C1-C10 hydrocarbon group; and $R^1$ is allowed to have a substituent therein and to contain an atom other than carbon in a structure thereof.

In the present invention, the carbonyl compound only needs to be a compound having a carbonyl group, and examples of the carbonyl compound include aldehyde compounds and ketone compounds. Further, in the present invention, the aldehyde compound is a compound having an aldehyde group within a molecule, and the cyanohydrin compound is a compound having a cyano group and a hydroxyl group within a molecule. The present invention has as an object, in particular, to produce a cyanohydrin compound (α-cyanohydrin) having a cyano group and a hydroxyl group both attached to an identical carbon atom.

Since examples of the carbonyl compound in the production process according to the present invention include aldehyde compounds as mentioned above, the aldehyde compounds are described first.

(Aldehyde Compound)

Those aldehyde compounds which are used in the present invention are carbonyl compounds, represented by general formula (1) above, which have at least one hydrogen atom in a carbonyl group thereof (i.e., which have a formyl group). The inventors have found that when an aldehyde compound or, in particular, one having a small carbon number is used in producing a cyanohydrin compound by reacting the aldehyde compound with hydrogen cyanide, the resulting cyanohydrin compound is prone to react with an unreacted portion of the aldehyde compound and therefore low in reaction yield. Therefore, the present invention brings about a particularly significant effect when that one of the aforementioned aldehyde compounds which has a small carbon number is used.

That is, the present invention makes it possible to produce a cyanohydrin compound in good yield, in particular, by reacting an aldehyde compound having a small carbon number or, in particular, one having a C1-C3 hydrocarbon group with hydrogen cyanide. Those aldehyde compounds which are used in the present invention are preferably aldehyde compounds that are small in carbon number, and examples of such aldehyde compounds include, but are not limited to: saturated alkylaldehydes such as formaldehyde, acetoaldehyde, and propionaldehyde; unsaturated alkylaldehydes such as acrylaldehyde, methacrylaldehyde, and propiolaldehyde; and aromatic aldehydes such as benzaldehyde, naphthoaldehyde, phthalaldehyde, and nicotinaldehyde. Further, these aldehydes may have a substituent such as amine, amide, methoxy, phenyl, nitro, hydroxyl, aldehyde, or carboxylic acid. When an aldehyde that is used in the present invention is solid at ambient temperature, it is possible to use the aldehyde after dissolving or suspending it in a solvent that is inactive against the reaction.

(Ketone Compound)

Other than aldehyde compounds, examples of the carbonyl compound in the production process according to the present invention include ketone compounds. Ketone compounds that can be used in the present invention only need to have a ketone group, and examples of such ketone compounds include acetone, 2-butanone, 2-pentanone, 3-methyl-2-butanone, 3-pentanone, 3-hexanone, 2-methyl-3-pentanone, 3-heptanone, 2-methyl-3-hexanone, 2,4-dimethyl-3-pentanone, acetophenone, 2-nonanone, 2-octanone, 2-heptanone, 2-hexanone, 4-methyl-2-pentanone, 4-heptanone, cyclohexanone, and 2,6-dimethyl-4-heptanone.

(Hydrogen Cyanide)

As the hydrogen cyanide that is used in the present invention, (a) hydrogen cyanide obtained by the ammonium oxidization of methane, (b) hydrogen cyanide produced by acidifying lithium cyanide, sodium cyanide, potassium cyanide, calcium cyanide, or the like with hydrochloric acid or sulfuric acid, or (c) hydrogen cyanide purified by distilling either (a) or (b) can be used. Further, because the hydrogen cyanide is unstable, it is possible to use hydrogen cyanide containing an acidic stabilizer such as sulfur dioxide.

(Catalyst)

As the catalyst that is used in the production process according to the present invention, a basic catalyst is used. As the basic catalyst, either an organic basic compound or an inorganic basic compound can be used. Among them, the organic basic compound is preferred. Examples of those compounds which are used as the catalyst include: tertiary amino compounds such as trimethylamine, triethylamine, tripropylamine, triisopropylamine, tributylamine, triheptylamine, trioctylamine, 1,4-diazabicyclo[2,2,2]octane, N-methylpyrrolidine, N-methylpiperidine, N-methylmorpholine, and N,N-dimethylaniline; metal alcoholate compounds such as lithium methoxide, lithium ethoxide, lithium propoxide, lithium butoxide, sodium methoxide, sodium ethoxide, sodium propoxide, sodium butoxide, potassium methoxide, potassium ethoxide, potassium propoxide, and potassium butoxide; alkali metal compounds and alkaline-earth metal compounds such as lithium hydroxide, sodium hydroxide, potassium hydroxide, calcium hydroxide, magnesium hydroxide, lithium carbonate, sodium carbonate, potassium carbonate, calcium carbonate, and magnesium carbonate; and basic compounds such as basic ion-exchange resin and zeolite.

It is preferable that the proportion of such a catalyst that is used be 0.001 to 0.1 mol, more preferably 0.003 to 0.05 mol, or even more preferably 0.005 to 0.01 mol with respect to 1 mol of the hydrogen cyanide. It is undesirable that the proportion of the catalyst that is used be less than 0.001 mol with respect to 1 mol of the hydrogen cyanide, because when the proportion is less than 0.001 mol, the reaction between the carbonyl compound such as the aldehyde compound and the hydrogen cyanide slows down, an unreacted portion of the carbonyl compound such as the aldehyde compound remains, and it becomes difficult to control the content of the carbonyl compound such as the aldehyde compound within a particular range. On the other hand, it is undesirable that the proportion of the catalyst be greater than 0.1 mol, because when the proportion is greater than 0.1 mol, that large portion of the catalyst which was not used in the reaction remains in the reaction system and polymerization of the hydrogen cyanide tends to take place.

Further, when the hydrogen cyanide that is used contains an acidic stabilizer, the reaction between the basic compound and the acidic stabilizer may cause loss of catalytic activity. In order to prevent such loss, it is only necessary to add to the basic compound in an amount equivalent in number of contained moles to the stabilizer. The proportion of the catalyst is an effective amount of the catalyst after such offsetting. When the basic compound is solid at room temperature, it is only necessary to use the basic compound after dissolving or suspending it either in the carbonyl compound such as the aldehyde compound or in the solvent.

(Solvent)

In the production process according to the present invention, it is possible to use the solvent that is inactive to the reaction between the carbonyl compound such as the aldehyde compound and the hydrogen cyanide. When the carbonyl compound or the catalyst is solid at reaction temperature, these substances can be used after dissolving or suspending them in the solvent.

Usable examples of the solvent in the present invention include: aliphatic hydrocarbon solvents such as pentane, hexane, heptane, and octane; alicyclic hydrocarbon solvents such as cyclopentane, cyclohexane, cycloheptane, and cyclooctane; aromatic hydrocarbon solvents such as benzene, toluene, and xylene; halogenated hydrocarbon solvents such as dichloromethane, chloroform, tetrachloromethane, dichloroethane, and chlorobenzene; and ether solvents such as diethyl ether, diisopropyl ether, methyl-t-butyl ether, dibutyl ether, and tetrahydrofuran. In the case of use of, e.g., toluene as a solvent in producing an α-hydroxyester compound with use of a cyanohydrin compound produced by the present invention, it is preferable to use toluene as a solvent also in producing the cyanohydrin compound. In this case, the cyanohydrin compound does not need to be isolated; therefore, the total amount of the cyanohydrin compound thus obtained can be effectively used.

The amount of the solvent that is used only needs to be appropriately either such an amount that the carbonyl compound, such as the aldehyde compound, which is used as a raw material, the basic compound, which is used as the catalyst, or the cyanohydrin compound, which is the product, can be dissolved, or such an amount that a solution in which these substances have been suspended exhibits fluidity.

(Reaction)

In the production process according to the present invention, the reaction between the carbonyl compound and the hydrogen cyanide is a reaction represented by reaction formula (2), when explained by taking as an example the aldehyde compound represented by general formula (1), in which the cyanohydrin compound is produced through the addition to the aldehyde compound represented by general formula (1) of hydrogen cyanide activated by the catalyst.

[Chem. 3]

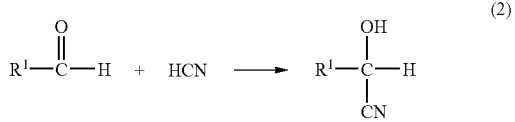

(2)

wherein $R^1$ is an aryl group or a C1-C10 hydrocarbon group; and $R^1$ is allowed to have a substituent therein and to contain an atom other than carbon in a structure thereof.

In the production process according to the present invention, it is preferable that the content of the carbonyl compound such as the aldehyde compound in the reaction system be not more than 50 mol %, more preferably not more than 20 mol %, or even more preferably not more than 5 mol % with respect to the intended cyanohydrin compound. However, the hydrogen cyanide must be used in a range of 0.9 to 3.0 mol with respect to 1 mol of the carbonyl compound such as the aldehyde compound before the cyanohydrin compound flows out of the reaction system. Furthermore, it is more preferable that the hydrogen cyanide be 1.0 to 2.0 mol or even more preferably 1.0 to 1.5 mol with respect to 1 mol of the carbonyl compound such as the aldehyde compound. The reaction system here refers to a system that is used between (a) mixing the carbonyl compound such as the aldehyde compound and the hydrogen cyanide together and (b) stopping the reaction by either isolating the cyanohydrin compound or neutralizing or removing the basic catalyst, or that is used in a reaction in the next step. Specifically, for example, when a carbonyl compound such as an aldehyde compound is supplied into a solution containing hydrogen cyanide and a catalyst in advance, the reaction system refers to the solution. Further, also when a catalyst and a carbonyl compound such as an aldehyde compound are supplied into a solution containing hydrogen cyanide, the reaction system refers to the solution into which the catalyst and the carbonyl compound such as the aldehyde compound have been supplied. That is, in the present invention, the reaction is made to proceed so that the concentration of the carbonyl compound such as the aldehyde compound in the solution is not more than 50 mol % with respect to the intended product, i.e., the cyanohydrin compound.

The following describes examples of methods for reaction in which the concentration of a carbonyl compound such as an aldehyde compound in a reaction system is adjusted as stated above.

A first method is for example a method that involves the supply of a carbonyl compound such as an aldehyde compound into a reactor vessel into which hydrogen cyanide has been fed in advance. In this case, it is preferable that the hydrogen cyanide be dissolved in advance in a solvent, because the dissolution of the hydrogen cyanide in the solvent makes it easy to control the reaction temperature and the pH.

A second method involves the simultaneous supply of a carbonyl compound such as an aldehyde compound and hydrogen cyanide into a reactor vessel. It should be noted here that the amount to be supplied only needs to be controlled so that the concentration of the carbonyl compound such as the aldehyde compound in the reaction system falls within the range. Therefore, the second process can take various forms of supply. Examples include alternate and separate supply of the carbonyl compound such as the aldehyde compound and the hydrogen cyanide and simultaneous supply of both the raw materials. Further, in the second process, it is preferable that a solvent be fed in advance into the reactor vessel. Such use of a solvent makes it possible to stir the reaction liquid, and to therefore adjust various reaction conditions such as reaction temperature and pH.

Further, it is preferable that the temperature inside of the reaction system of the carbonyl compound such as the aldehyde compound and the hydrogen cyanide be controlled to be kept at −10 to 60° C. It is more preferable that the temperature inside of the reaction system be 0 to 40° C. or even more preferably 10 to 20° C. It is undesirable that the temperature inside of the reaction system be not higher than −10° C., because at such a low temperature the reaction between the carbonyl compound such as the aldehyde compound and the hydrogen cyanide slows down; moreover, a high-performance freezing machine is required, i.e., a lot of energy is required for cooling. On the other hand, it is undesirable that the temperature inside of the reaction system be not lower than 60° C., because at such a high temperature the resulting cyanohydrin compound is thermally decomposed or the hydrogen cyanide becomes prone to be dispersed to entail risks.

As a method for cooling the inside of the reaction system, a publicly known technique can be adopted. Examples of such a method include: immersing the reactor vessel in a refrigerant such as a water bath; and providing a jacket or the like around the reactor and circulating a refrigerant through the jacket. Further, as a method for controlling the temperature inside of the reactor, a publicly known method can be used. Examples of such a method include: controlling the temperature from the outside of the reactor by regulating the temperature of a refrigerant with the supply of the raw materials held constant; and controlling the temperature inside of the reaction system by controlling the calorific value through a change in supply of the raw materials with the refrigerant temperature held constant. Further, these control methods may be used in combination.

Usable examples of the refrigerant that is used include: coolant water chilled by a cooling tower; and a refrigerant (an aqueous solution of ethylene glycol and calcium chloride) chilled by use of a freezing machine. Among them, it is preferable to use a refrigerant chilled by a freezing machine. Further, needless to say, the lower the refrigerant temperature is, the larger the amount of production per unit time is.

A cyanohydrin compound obtained by the process according to the present invention for producing a cyanohydrin compound may be either purified by a publicly known method such as distillation or column chromatography or used as it is without purification in a reaction such as production of an α-hydroxyester compound.

A cyanohydrin compound that is produced by the process according to the present invention for producing a cyanohydrin compound is an organic compound having a cyanide ion added to the carbonyl group of the carbonyl compound such as the aldehyde compound, and sometimes referred to as "cyanhydrin compound". Examples of cyanohydrin compounds that can be suitably produced by the present invention include, but are not limited to: saturated alkylhydroxynitriles such as hydroxyacetonitrile, lactonitrile, and α-hydroxybutanenitrile; unsaturated alkylhydroxynitriles such as α-hydroxybuta-3-ennitrile, α-hydroxy-3-methylbuta-3-ennitrile, and α-hydroxybuta-3-innitrile; aromatic alkylhydroxynitriles such as mandelonitrile, hydroxy(2-naphthyl)acetonitrile, (3-(cyano(hydroxy)methyl)phenyl))(hydroxy)acetonitrile, and hydroxy(pyridine-3-yl)acetonitrile. Further, these cyanohydrin compounds may have a substituent such as amine, amide, methoxy, phenyl, nitro, hydroxyl, aldehyde, or carboxylic acid.

The production process according to the present invention makes it possible to reduce the existential quantity of an unreacted portion of the carbonyl compound such as the aldehyde compound in the reaction system. This makes it possible, as a result, to inhibit the resulting cyanohydrin compound from reacting with the carbonyl compound such as the aldehyde compound, and to therefore produce the cyanohydrin compound in good yield.

[Process for Producing an α-hydroxyester Compound]

The present invention also provides a process for producing an α-hydroxyester compound with use of a cyanohydrin compound produced by the production process according to the present invention.

In the process according to the present invention for producing an α-hydroxyester compound, a cyanohydrin compound obtained by the production process is used.

That is, the process according to the present invention for producing an α-hydroxyester compound includes the steps of: (i) obtaining a cyanohydrin compound by performing a reaction between a carbonyl compound such as an aldehyde compound and hydrogen cyanide in the presence of a basic catalyst under the condition that the content of the aldehyde compound in a reaction system is not more than 50 mol % with respect to the intended cyanohydrin compound; and (ii) hydrolyzing and esterifying the cyanohydrin compound.

When explained by taking as an example the aldehyde compound represented by general formula (1), the reaction in the step (i) is represented by reaction formula (2), and the reaction in the step (ii) is represented, for example, by reaction formula (3):

[Chem. 4]

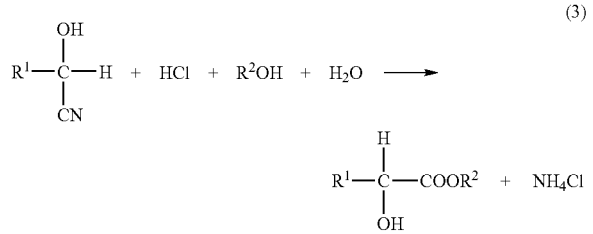

(3)

wherein $R^1$ and $R^2$ are independently an aryl group or a C1-C10 hydrocarbon group; and $R^1$ or $R^2$ is allowed to have a substituent therein and to contain an atom other than carbon in a structure thereof.

That is, the cyanohydrin compound can be hydrolyzed and esterified efficiently by introducing hydrochloric gas into a mixture of the cyanohydrin compound, alcohols, water, and a solvent. Examples of alcohols that can be used in this reaction include methanol, ethanol, n-propanol, i-propanol, n-butanol, s-butanol, n-heptanol, n-hexanol, n-octanol, 2-ethylhexanol, cyclohexanol, and benzyl alcohol. In the present invention, methanol, ethanol, n-propanol, i-propanol, and the like can be suitably used. Further, the reaction in the step (ii) is not limited to reaction formula (3) as long as it is a reaction in which the cyanohydrin compound can be hydrolyzed and esterified.

Ester compounds that can be suitably produced by the process according to the present invention for producing an ester compound are carboxylic acid esters that are produced by a reaction between carboxylic acid obtained from a cyanohydrin compound and alcohol, and examples of such esters include, but are not limited to: saturated alkylhydroxyesters such as methyl hydroxyacetate, methyl α-hydroxypropionate, and methyl α-hydroxybutyrate; unsaturated alkylhydroxyesters such as methyl α-hydroxybutenoate, methyl β-methyl-α-hydroxybutenoate, and methyl α-hydroxybutynoate; and aromatic hydroxyesters such as methyl mandelate, methyl hydroxy-2-naphthylacetate, methyl hydroxy(3-(1-hydroxy-2-methoxy-2-oxoethyl))phenylacetate, and methyl hydroxy(pyridine-3-yl)acetate. Further, these ester compounds may have a substituent such as amine, amide, methoxy, phenyl, nitro, hydroxyl, aldehyde, or carboxylic acid.

In the process according to the present invention for producing an α-hydroxyester compound, for example, with use of α-hydroxybutyronitrile produced by the process for producing a cyanohydrin compound, methyl α-hydroxybutyrate can be produced by hydrolyzing α-hydroxybutyronitrile and esterifying it with methanol.

The process according to the present invention for producing an α-hydroxyester compound makes it possible to produce an α-hydroxyester compound with use of a cyanohydrin compound produced in good yield. Therefore, when the α-hydroxyester compound is produced by using an equimolar amount of a carbonyl compound such as an aldehyde compound as a starting material, the α-hydroxyester compound can be produced in good yield in comparison with the conventional process. This makes it possible to realize a reduction in production cost of the α-hydroxyester compound.

EXAMPLES

The following describes Examples of the present inventions; however, the present invention is not restricted to the following Examples. In the present example and each of the examples below, the reaction yield of a cyanohydrin compound is denoted by the amount (mol %) of cyanohydrin compound production based on the amount of an aldehyde compound that is used in the reaction, and was calculated according to an absolute calibration method. The analysis condition was as follows: Column Inertsil CN-3 (4.6×250 mm 5 μm); Column temperature: 40° C.; Mobile phase Hexane:EtOH=95:5; Flow rate: 1.0 mL/min; Detector: RI (refractive index detector); Range: 8; Response: 5; Injection volume: 20 μL (fixed by a loop).

Example 1

Hydroxybutyronitrile (hereinafter referred to sometimes as "HBN") was produced by using, as a reactor, a 100-milliliter four-neck flask including a thermometer, a reflux condenser, and a stirrer. Into this reactor, 31.3 g of toluene were fed, and then cooled down to 10° C. A syringe pump was used to supply 35.3 g of 0.6 mol % triethylamine/propionaldehyde (0.6 mol-aldehyde) and 17.2 g of hydrogen cyanide (0.636 mol) over a two-hour period while keeping the temperature inside of the reactor at 10 to 20° C. Thus obtained was a reaction liquid. The reaction liquid was analyzed, whereby the reaction yield of HBN was found to be 96 mol %, with no propionaldehyde detected.

Example 2

HBN was produced by using, as a reactor, a 200-liter SUS reaction pot including a thermometer, a reflux condenser, and a stirrer. Into this reaction pot, 40.6 L of toluene and 0.2 kg of triethylamine (0.6 mol-aldehyde) as a catalyst were fed, and then cooled down to 10° C. While keeping the temperature inside of the pot at 10 to 20° C., 20.46 kg of propionaldehyde (352 mol) and 10.0 kg of hydrogen cyanide (370 mol, in an equivalent amount of 1.05 to aldehyde) were supplied over a three-hour period. The reaction liquid thus obtained was analyzed, whereby the reaction yield of HBN was found to be 96 mol %, with no propionaldehyde detected.

Example 3

HBN was produced by using, as a reactor, a 3.5 m³ glass lining reaction pot including a thermometer, a reflux condenser, and a stirrer. Into this reaction pot, 1,000 L of toluene and 12.6 kg of triethylamine (0.6 mol %-aldehyde) as a catalyst were fed. After they were cooled down to 10° C., 1210.6 kg of propionaldehyde (20.8 kmol, in an equivalent amount of 1.05 to aldehyde) and 589.7 kg of hydrogen cyanide (21.84 kmol, in an equivalent amount of 1.05 to aldehyde) were cooled down as much as possible with use of brine of approximately −18° C., and then simultaneously supplied over a sixteen-hour period while keeping the temperature inside of the reaction system at 10 to 20° C. The reaction liquid thus obtained was analyzed, whereby the reaction yield of HBN was found to be 96 mol %, with no propionaldehyde detected.

Example 4

Lactonitrile was produced by using, as a reactor, a 100-milliliter four-neck flask including a thermometer, a reflux condenser, and a stirrer. This reactor was cooled down to 10° C., and a syringe pump was used to simultaneously supply 23.0 g of 1.0 mol % triethylamine/acetoaldehyde (0.51 mol.aldehyde) and 14.5 g of hydrogen cyanide (0.54 mol) over a two-hour period while keeping the temperature inside of the pot at 5 to 10° C. The reaction liquid thus obtained was analyzed, whereby the reaction yield of lactonitrile was found to be 99 mol %, with no acetoaldehyde detected.

Example 5

Mandelonitrile was produced by using, as a reactor, a 100-milliliter four-neck flask including a thermometer, a reflux condenser, and a stirrer. This reactor was cooled down to 10° C., and a syringe pump was used to simultaneously supply 50.2 g of 1.0 mol % triethylamine/benzaldehyde (0.47 mol.aldehyde) and 13.4 g of hydrogen cyanide (0.49 mol) over a two-hour period while keeping the temperature inside of the pot at 20 to 25° C. The reaction yield of the reaction liquid was analyzed by HPLC, whereby a large amount of benzaldehyde was found to be remaining. Therefore, 6.0 g of hydrogen cyanide 0.22 mol) were added. After that, the reaction liquid thus obtained was analyzed, whereby the reaction yield of mandelonitrile was found to be 95 mol %, with no benzaldehyde detected.

Reference Example

HBN was produced by using, as a reactor, a 100-milliliter four-neck flask including a thermometer, a reflux condenser, and a stirrer. Into this reactor, 9.9 g of hydrogen cyanide (0.37 mol) and 0.08 g of triethylamine were fed, and then cooled down to 10° C. or lower. While keeping a temperature of 0 to 10° C., 6.8 g of 0.6 mol % triethylamine/propionaldehyde (0.12 mol-aldehyde) were supplied over a 25-minute period. A temperature of 10° C. was kept for eighteen hours. After that, at the same temperature, 13.5 g of 0.6 mol % triethylamine/propionaldehyde (0.23 mol-aldehyde) were supplied over a twenty-minute period. The reaction liquid thus obtained was analyzed, whereby the reaction yield of HBN was found to be 94 mol %, with no propionaldehyde detected.

Example 7

HBN was produced by using, as a reactor, a 200-milliliter four-neck flask including a thermometer, a reflux condenser, and a stirrer. Into this, reactor, 60.0 g of toluene and 0.33 g of triethylamine (0.6 mol %—with respect to propionaldehyde) were fed. Then, 20.9 g of propionaldehyde (0.360 mol) and 8.5 g of hydrogen cyanide (0.313 mol) (hydrogen cyanide/propionaldehyde=0.87 mol/mol) were simultaneously supplied over a one-hour period. After that, 13.9 g of propionaldehyde (0.240 mol) and 8.5 g of hydrogen cyanide (0.313 mol) (hydrogen cyanide/propionaldehyde=1.30 mol/mol) were simultaneously supplied over a one-hour period. The reaction liquid thus obtained was analyzed, whereby the reaction yield of HBN was found to be 96 mol %, with no propionaldehyde detected.

Example 8

Into a 500-milliliter four-neck flask equipped with a thermometer, a reflux condenser, and a stirrer, 187.4 g of the HBN reaction liquid obtained in Example 2 (HBN yield 96%, 1.0 mol scale-aldehyde) were fed. After the addition of 100.9 g of methanol (3.15 mol) and 19.5 g of water (1.08 mol), the internal temperature was adjusted to 20° C. After blowing of 41.89 g of hydrogen chloride (1.15 mol) maintained at 38±2° C. and then eight hours of reflux maturation, a reaction liquid containing α-hydroxybutanoic ester was obtained. The yield was analyzed by gas chromatograph with toluene held constant, whereby the reaction yield of α-hydroxybutanoic ester was found to be 85.3 mol %.

Comparative Example 1

HBN was produced by using, as a reactor, a 3.5 m 3 glass lining reaction pot including a thermometer, a reflux condenser, and a stirrer. Into this reactor, 1210.6 kg of propionaldehyde (20.8 kmol) (with a purity of not less than 98%) and 11.2 kg of triethylamine (0.11 kmol) as a catalyst were fed, and then cooled down to approximately 10° C. while being stirred. While the temperature inside of the reactor was kept at approximately 10 to 20° C. by cooling down the reactor as much as possible with use of brine of approximately −18° C., 587.1 kg of hydrogen cyanide (21.7 kmol) were supplied into the reactor over an eighteen-hour period. The resultant reaction liquid was analyzed, whereby the reaction yield of HBN was found to be 85 mol %.

Comparative Example 2

HBN was produced by using, as a reactor, a 300-milliliter four-neck flask including a thermometer, a reflux condenser, a stirrer, and a dropping funnel. Into this reactor, 145.2 g of propionaldehyde (2.50 mol; with a purity of not less than 98%) and 1.5 g of triethylamine (15 mmol) as a catalyst were fed, and then cooled down to approximately 15° C. while being stirred. While the temperature inside of the reactor was kept at 10 to 20° C., 23.5 g of hydrogen cyanide (0.87 mol) were supplied into the reactor over a forty-minute period. After the temperature was held within the range for 23 hours, 46.9 g of hydrogen cyanide (1.74 mol) were further supplied into the reactor over an eighty-minute period. The resultant reaction liquid was analyzed, whereby the reaction yield of HBN was found to be 87 mol %.

Comparative Example 3

HBN was produced through the batch process by using, as a reactor, a 300-milliliter four-neck flask including a thermometer, a reflux condenser, a stirrer, and a dropping funnel. Into this reactor, 145.2 g of propionaldehyde (2.50 mol; with a purity of not less than 98%) and 1.5 g of triethylamine (15 mmol) as a catalyst were fed, and then cooled down to 25° C. while being stirred. While the temperature inside of the reactor was kept at 20 to 30° C., 23.5 g of hydrogen cyanide (0.87 mol) were supplied into the reactor over a thirty-minute period. After the temperature was held within the range for nineteen hours, 46.9 g of hydrogen cyanide (1.74 mol) were further supplied into the reactor over an eighty-minute period. The resultant reaction liquid was analyzed, whereby the reaction yield of HBN was found to be 79 mol %.

Comparative Example 4

Into a 100-milliliter four-neck flask including a thermometer, a reflux condenser, a dropping funnel, and a stirrer, 42.4 g of benzaldehyde (0.40 mol) and 0.2 g of triethylamine (1.6 mmol, 0.4 mol % with respect to aldehyde) as a catalyst were fed, and then cooled down to not higher than 20° C. while stirring. While the temperature inside of the reactor was kept at 20 to 30° C., 3.8 g of hydrogen cyanide (0.14 mol) were dropped over a ten-minute period. After that, a temperature of 25° C. was kept for 22 hours. On this occasion, a crystal considered to be a by-product was found in the reaction liquid. After that, 7.6 g of hydrogen cyanide (0.29 mol) were dropped over a thirty-minute period. The resultant reaction liquid was analyzed, whereby the reaction yield of mandelonitrile was found to be 83 mol %.

Comparative Example 5

Lactonitrile was produced by using, as a reactor, a 200-milliliter four-neck flask including a thermometer, a reflux condenser, dropping funnel, and a stirrer. Into this reactor, 44.1 g of acetaldehyde (1.00 mol; with a purity of not less than 98%) and 1.0 g of triethylamine (10 mmol, 1.0 mol % with respect to aldehyde) as a catalyst were fed, and then cooled down to 10° C. while being stirred. While the temperature inside of the reactor was kept at 0 to 10° C., 8.5 g of hydrogen cyanide (0.31 mol) were supplied into the reactor over a 25-minute period. After a temperature of 10° C. was kept for fifteen hours, 19.9 g of hydrogen cyanide (0.73 mol) were further supplied into the reactor over a sixty-minute period. The resultant reaction liquid was analyzed, whereby the reaction yield of lactonitrile was found to be 61 mol %.

Comparative Example 6

A reaction liquid containing α-hydroxybutanoic ester was obtained in the same manner as in Example 7, except that the reaction liquid obtained in Comparative Example 1 was used. The reaction liquid was analyzed in the same manner, whereby the reaction yield of α-hydroxybutanoic ester based on the amount of propionaldehyde was found to be 76.0 mol %.

As shown by comparing Examples 1 to 5 and Comparative Examples 1 to 5, it was confirmed that the production process according to the present invention can produce a desired cyanohydrin compound in good yield in each case. Further, as shown by comparing Example 8 and Reference Example 6, it was confirmed that the present example can produce an α-hydroxyester compound in good yield.

The process according to the present invention for producing a cyanohydrin compound makes it possible to reduce the existential quantity of an unreacted portion of the carbonyl compound such as the aldehyde compound in the reaction system, and to therefore inhibit a reaction between this carbonyl compound and cyanohydrin. This makes it possible, as a result, to produce cyanohydrin in better yield.

Further, a process according to the present invention for producing an α-hydroxyester compound makes it possible produce an intermediate, i.e. a cyanohydrin compound in good yield, considered in relation to a starting material, i.e. a carbonyl compound such as an aldehyde compound, and to therefore produce a final product, i.e. an α-hydroxyester compound in good yield.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

A cyanohydrin compound produced by a production process according to the present invention is useful as a starting material for various compounds, and the present invention makes it possible to produce a cyanohydrin compound in good yield. Therefore, the present invention is widely applicable in the pharmaceutical industry, the agrichemical industry, and the like.

The invention claimed is:
1. A process for producing a cyanohydrin compound by performing a reaction between a carbonyl compound and hydrogen cyanide in the presence of a catalyst through a batch process,
the process comprising the step of controlling a content of the carbonyl compound in a reaction system to not more than 50 mol % with respect to the cyanohydrin compound,
the reaction between the hydrogen cyanide and the carbonyl compound being performed by either simultaneously or separately supplying the hydrogen cyanide and the carbonyl compound into a reactor vessel.
2. The process as set forth in claim 1, wherein the carbonyl compound is an aldehyde compound represented by general formula (1):

[Chem. 1]

(1)

wherein $R^1$ is an aryl group or a C1-C10 hydrocarbon group; and $R^1$ is allowed to have a substituent therein and to contain an atom other than carbon in a structure thereof.

3. The process as set forth in claim 1, wherein the hydrogen cyanide is used in a range of 0.9 to 3.0 mol with respect to 1 mol of the carbonyl compound before the cyanohydrin compound flows out of the reactor vessel.

4. The process as set forth in claim 1, wherein the catalyst is at least either an organic basic compound or an inorganic basic compound.

5. The process as set forth in claim 3, wherein the catalyst is a compound selected from the group consisting of an amine compound, an aromatic amine compound, an alkali metal compound, a metal alkoxide compound, and an alkaline-earth metal compound.

6. The process as set forth in claim 1, wherein the catalyst is used in a range of 0.001 to 0.1 mol with respect to 1 mol of the hydrogen cyanide.

7. A process for producing an α-hydroxyester compound, the process comprising the step of hydrolyzing and esterifying a cyanohydrin compound produced by a process as set forth in claim 1.

* * * * *